United States Patent
Fox

(10) Patent No.: US 9,863,864 B2
(45) Date of Patent: Jan. 9, 2018

(54) THRESHOLD SELECTOR FOR FLOW CYTOMETER

(71) Applicant: Bio-Rad Laboratories, Inc., Hercules, CA (US)

(72) Inventor: Daniel Nelson Fox, Bellvue, CO (US)

(73) Assignee: Bio-Rad Technologies, Inc., Hercules, CA (US)

( * ) Notice: Subject to any disclaimer, the term of this patent is extended or adjusted under 35 U.S.C. 154(b) by 0 days.

(21) Appl. No.: 15/264,326

(22) Filed: Sep. 13, 2016

(65) Prior Publication Data

US 2017/0074776 A1 Mar. 16, 2017

Related U.S. Application Data

(60) Provisional application No. 62/219,049, filed on Sep. 15, 2015.

(51) Int. Cl.
*G01N 21/00* (2006.01)
*G01N 15/14* (2006.01)
*G01N 15/10* (2006.01)

(52) U.S. Cl.
CPC ....... *G01N 15/1429* (2013.01); *G01N 15/147* (2013.01); *G01N 15/1425* (2013.01); *G01N 2015/1006* (2013.01)

(58) Field of Classification Search
CPC .......... G01N 15/1429; G01N 15/1425; G01N 21/00; G01N 21/6428
USPC ....................................................... 356/343
See application file for complete search history.

(56) References Cited

U.S. PATENT DOCUMENTS

| | | | |
|---|---|---|---|
| 5,150,313 A | | 9/1992 | Van Den Engh et al. |
| 2008/0221812 A1* | | 9/2008 | Pittaro ................... G01N 15/14 702/66 |
| 2011/0303859 A1 | | 12/2011 | Lofstrom et al. |
| 2015/0253235 A1 | | 9/2015 | Kaduchak et al. |
| 2017/0045436 A1 | | 2/2017 | Fox et al. |

OTHER PUBLICATIONS

International Search Report and Written Opinion dated Dec. 8, 2016 in International Application No. PCT/US2016/051970.
Flow Cytometry Basics Guide. Bio-Rad. Online Guide. Dec. 8, 2015, 48 pages. [retrieved Nov. 4, 2016] <URL:https://vvww.bio-rad-antibodies.com/static/2015/resources-2015/fc/flowcytometry.pdf.>.
U.S. Appl. No. 62/204,001, filed Aug. 12, 2015, Fox et al.

* cited by examiner

*Primary Examiner* — Roy M Punnoose
(74) *Attorney, Agent, or Firm* — Weaver Austin Villeneuve & Sampson LLP

(57) ABSTRACT

Disclosed is a threshold selector that selects a threshold by generating a histogram from a detector signal and a flow cytometer. The detector signal includes both data and noise. A histogram is generated, which includes height data from the pulses of the detector signal as well as noise. The flow cytometer can be operated without samples to generate a histogram that includes only noise. The threshold signal can then be selected by selecting an intensity level on the histogram that is between the noise and data.

19 Claims, 10 Drawing Sheets

(700 Threshold set too low)

(800 Threshold set correctly)

(900 Threshold set too high)

In Figures 7-8, the horizontal axis shows two sets of values—the lower value represents the actual, non-logarithmically scaled value of the detector signal, and the upper value represents the logarithmically quantized 8-bit value of the detector signal.

In Figures 10 and 11, the horizontal axis shows two sets of values—the lower value represents the actual, non-logarithmically scaled value of the detector signal, and the upper value represents the logarithmically quantized 8-bit value of the detector signal.

THRESHOLD SELECTOR FOR FLOW CYTOMETER

CROSS REFERENCE TO RELATED APPLICATIONS

This application claims benefit of priority under 35 U.S.C. §119(e) to U.S. Provisional Patent Application No. 62/219,049, filed Sep. 15, 2015 and titled "THRESHOLD GENERATOR FOR FLOW CYTOMETER," which is hereby incorporated by reference herein in its entirety.

BACKGROUND

Flow cytometers are useful devices for analyzing and sorting various types of particles in fluid streams. These cells and particles may be biological or physical samples that are collected for analysis. The sample is mixed with a sheath fluid for transporting the particles through the flow cytometer. The particles may comprise biological cells, calibration beads, physical sample particles, or other particles of interest. Analysis of these particles can provide valuable information to both researchers and clinicians.

SUMMARY

The systems, methods and devices of this disclosure each have several innovative aspects, no single one of which is solely responsible for the desirable attributes disclosed herein. Included among these aspects are at least the following implementations, although further implementations may be set forth in the detailed description or may be evident from the discussion provided herein.

In some implementations, a flow cytometry apparatus is provided that includes a detector configured to produce a detector signal responsive to detecting light during operation of the flow cytometer; a first pulse processor configured to receive the detector signal from the detector and to output detector data characterizing pulse heights of pulses in the detector signal; and a second pulse processor configured to also receive the detector signal from the detector and to output a pulse height data signal, a pulse width data signal, and a pulse area data signal for desired pulses in the detector signal. The second pulse processor may be configured to output the pulse height data signal, the pulse width data signal, and the pulse area data signal for that desired pulse responsive to a set of one or more trigger conditions being met for each pulse. The set of one or more trigger conditions may at least include a trigger condition involving a comparison of the pulse height for that desired pulse with a trigger threshold value. The apparatus may further include a real-time trigger module configured to receive the detector data from the first pulse processor and to generate periodic histogram data from the detector data, and a threshold selector configured to receive the periodic histogram data from the real-time trigger module and to provide the trigger threshold value to the second pulse processor.

In some such implementations of the flow cytometry apparatus, the set of one or more trigger conditions may be met for each desired pulse when the pulse height for that desired pulse meets or exceeds the trigger threshold value.

In some additional or alternative such implementations, the first pulse processor may be configured to output the detector data characterizing the pulse height of the pulses in the detector signal only for pulses that meet or exceed a baseline trigger value.

In some implementations of the flow cytometry apparatus, the apparatus may further include a data storage device, and the flow cytometry apparatus may be configured to store the pulse height data signal, the pulse width data signal, and the pulse area data signal output by the second pulse processor on the data storage device. In some such implementations, the flow cytometry apparatus may be configured such that data from the first pulse processor is not stored on the data storage device. In some further such implementations, the data from the first pulse processor is not stored at all after it has been analyzed by the real-time trigger module and is instead discarded.

In some implementations of the flow cytometry apparatus, the apparatus may further include one or more additional detectors and one or more additional second pulse processors. In such implementations, each additional detector may be configured to produce a corresponding additional detector signal responsive to detecting light during operation of the flow cytometer, and each additional second pulse processor may be associated with a different one of the one or more additional detectors and may be configured to receive the corresponding additional detector signal from that additional detector and to output at least a corresponding additional pulse height data signal, a corresponding additional pulse width data signal, and a corresponding additional pulse area data signal responsive to each time the set of one or more trigger conditions is met.

In some further such implementations of the flow cytometry apparatus, the apparatus may further include an additional first pulse processor configured to receive the corresponding additional detector signal from a particular one of the one or more additional detectors and to output additional detector data characterizing pulse heights of pulses in that corresponding additional detector signal; the apparatus may also include an additional real-time trigger module configured to receive the additional detector data from the additional first pulse processor and to generate additional periodic histogram data from the additional detector data. In such an implementation, the threshold selector may be further configured to receive the additional periodic histogram data from the additional real-time trigger module and to provide an additional trigger threshold value, and the set of one or more trigger conditions may further include a trigger condition involving a comparison of a pulse height in the corresponding additional detector signal from the particular one of the one or more additional detectors with the additional trigger threshold value.

In some such implementations of the flow cytometry apparatus, the set of one or more trigger conditions may be met for each desired pulse when the pulse height for that desired pulse meets or exceeds the trigger threshold value and the pulse height in the corresponding additional detector signal from the particular one of the one or more additional detectors meets or exceeds the additional trigger threshold value during that desired pulse.

In some alternative such implementations of the flow cytometry apparatus, the set of one or more trigger conditions may be met for each desired pulse when a logic statement evaluates to true, the logic statement involving one or more Boolean operators, an evaluation of whether the pulse height for that desired pulse met or exceeded the trigger threshold value, and an evaluation of whether the pulse height in the corresponding additional detector signal from the particular one of the one or more additional detectors met or exceeded the additional trigger threshold value during that desired pulse. The one or more Boolean operators may be an AND operator, an OR operator, or a NOT operator, and combinations thereof.

In some implementations of the flow cytometry apparatus, the real-time trigger module may include a logarithmic converter, a state machine, a first RAM, and a second RAM. In such implementations, the logarithmic converter may be configured to convert the detector data into logarithmic detector data, the first RAM may store occurrence values, and each occurrence value may be associated with a different logarithmic pulse height value contained within the logarithmic detector data. Furthermore, the state machine may be configured to determine the logarithmic pulse height value for each pulse of the pulses represented in the logarithmic detector data during a first predetermined time period and cause, for each logarithmic pulse height value that is determined, the occurrence value associated with that logarithmic pulse height value to be incremented by one. The state machine may be further configured to cause the occurrence values stored in the first RAM at the end of the first predetermined time period to be copied to the second RAM and, subsequent to causing the occurrence values stored in the first RAM to be copied to the second RAM, cause the occurrence values stored in the first RAM to be re-set.

In some alternative or additional implementations of the flow cytometry apparatus, the apparatus may further include a display device, and the threshold selector may be configured to present the periodic histogram data on the display device, receive an input indicating a value for the trigger threshold value, and use the value indicated by the input as the trigger threshold value.

In some further such implementations of the flow cytometry apparatus, the apparatus may further include a memory, and the threshold selector may be configured to store occurrence values in the memory that are representative of one or more first instances of the periodic histogram data as a background noise template and then subtract the occurrence values of the background noise template from corresponding occurrence values in one or more second instances of the periodic histogram data generated after the one or more first instances of the periodic histogram data before presenting the one or more second instances of the periodic histogram data on the display device.

In some implementations of the flow cytometry apparatus, the threshold selector may be configured to automatically select the trigger threshold based on the periodic histogram data. In some such implementations, the threshold selector may be configured to automatically select the trigger threshold by applying one or more pattern recognition techniques to the periodic histogram data.

In some implementations of the flow cytometry apparatus, the real-time trigger module may be implemented in a field-programmable gate array or an application-specific integrated circuit.

In some implementations, a method if operating a flow cytometry system is provided. The method may include detecting light using a detector during operation of the flow cytometer, providing a detector signal from the detector to a first pulse processor configured to receive the detector signal, causing the first pulse processor to output detector data characterizing pulse heights of pulses in the detector signal, causing a real-time trigger module configured to receive the detector data from the first pulse processor to generate periodic histogram data from the detector data, causing a threshold selector configured to receive the periodic histogram data from the real-time trigger module to provide a trigger threshold value, and causing a second pulse processor configured to also receive the detector signal from the detector to output a pulse height data signal, a pulse width data signal, and a pulse area data signal for desired pulses in the detector signal. In such a method, the pulse height data signal, the pulse width data signal, and the pulse area data signal for each desired pulse are only output responsive to a set of one or more trigger conditions being met, and the set of one or more trigger conditions at least includes a trigger condition involving a comparison of the pulse height for that desired pulse with the trigger threshold value.

In some implementations of the method, the method may further include storing the pulse height data signal, the pulse width data signal, and the pulse area data signal for the desired pulses on a non-volatile storage device. In some further such implementations of the method, the method may further include discarding the detector data processed by the real-time trigger module without storing that data on the non-volatile storage device.

In some additional or alternative implementations of the method, the method may further include causing the threshold selector to display a histogram based on the periodic histogram data and a visual indicator on the histogram of the trigger threshold value.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

DETAILED DESCRIPTION OF THE EMBODIMENTS

Figure 1:
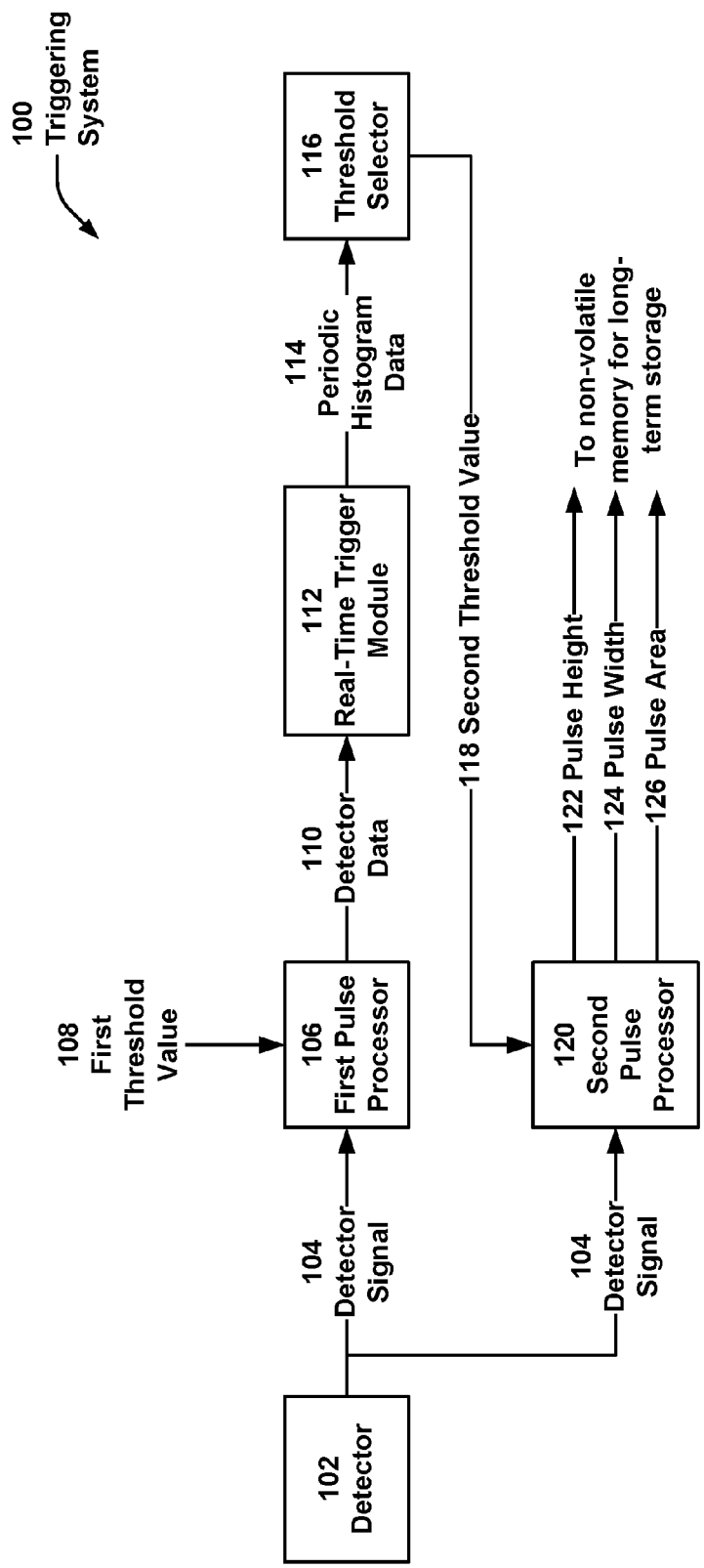
FIG. 1 is a schematic block diagram of an embodiment of a triggering system for use within a flow cytometer.

In many flow cytometry systems, particles of interest, e.g., cells, are tagged with fluorophores which are then optically stimulated in a sampling area or region of such systems using an excitation laser to produce fluorescence of a particular wavelength or range of wavelengths. This fluorescence, along with excitation source light scattered off of such particles, may be measured using highly sensitive photodetectors, e.g., photomultiplier tubes. Certain characteristics of the particles of interest may be determined based on the nature of the detected light. For example, if light of a fluorescence wavelength is detected, this may indicate the presence of a particle of interest in the sampling area or region at that time. Similarly, scattered excitation light that is detected may provide insight as to the morphology or size of the particle that is present in the sampling area or region at that time.

In a typical flow cytometry system, a liquid sample containing the particles of interest is flowed through a flow cell or out of a nozzle—and thus through a sampling area of the flow cytometer—on a generally continuous basis. Particles of interest, as well as other particles, debris, microbubbles, and other artifacts, thus pass through the sampling area and may produce a time-varying stream of photonic output (through fluorescence, scattering, or some other mechanism). In addition to these potential sources of light, the photodetectors that are used may also generate noise data that contributes to the detector signals produced by such photodetectors. Photonic events in the time-varying stream of photonic output may then be identified and classified in order to gain insight as to the nature of the analyzed sample.

Some modern flow cytometers may include as many as 40 photodetectors, e.g., photomultiplier tubes, each of which may have a very high bandwidth, e.g., in the 100's of megahertz. The signals from such analog detectors may then be filtered to the low megahertz range, e.g., 2-3 MHz, and then digitally sampled at frequencies ranging from 10 MHz to 50 MHz, depending on the flow cytometer. As a result, modern flow cytometers may be able to detect light from over 100,000 cells per second. The photodetectors used may also have a large dynamic range, e.g., spanning 5 decades, further increasing the amount of data that may be produced by such systems. If the data from such photodetectors was logged indiscriminately, the resulting data files from such flow cytometers would rapidly become unmanageable. For example, some high-end flow cytometry systems may have photodetectors that can detect over 250,000 events per second, with over 90 parameters being detected by the flow cytometer for each such event. If each such parameter has 4 bytes of data, for example, such systems may generate approximately 90 MB/s of data, which works out to more than 5 GB of data generated for each minute of analysis time.

To prevent the data logging systems of flow cytometers from becoming overwhelmed, it is common practice to set "triggers" or "thresholds" that cause a flow cytometer to log or process data only when the photodetectors produce data meeting certain minimum requirements—ideally data is only logged or processed when the data is believed to pertain to a particle of interest. The setting of these minimum requirements is somewhat difficult to do, as the exact values for such thresholds may differ based on the nature of the sample being analyzed, the fluorophores used, the optical filters present in the analysis system, and various other factors. Trigger or threshold setting must generally be performed by trial and error, and is therefore viewed as somewhat of an art form that is either intuitive or must be learned through practice.

When a measurement obtained from a detector or sensor meets the threshold value, the data from that detector or sensor may be stored or analyzed further, as discussed herein, but the data from other sensors or detectors may also be simultaneously stored or analyzed as well. Thus, the threshold value may act as a trigger for taking a data snapshot across all sensors of the flow cytometer when a particle of interest is deemed to be indicated in the detector signal using the threshold value.

Proper threshold setting is important in flow cytometry—if the threshold is set too low, this may cause a large number of records to be recorded that are produced by noise or other undesirable causes, as opposed to the particles of interest. This burdens the processing systems of the flow cytometer, increases the data file size, and makes it more difficult to analyze the resulting data. If the threshold is set too high, then this may cause not only "noise" to be omitted from the dataset, but may also cull out some of the particles of interest from the dataset, resulting in an inaccurate analysis of the sample.

The threshold, once selected, may be provided to a pulse processor that processes signals produced by the detectors. The pulse processor may analyze the received detector signals to identify pulses in the signals and may then extract pulse width, pulse height, and pulse area for pulses that meet the selected threshold, e.g., if the threshold is a particular intensity level of detected light, then the pulse width, height, and area for pulses having at that pulse height or higher may be logged. The extracted pulse information may then be stored by the flow cytometry system as part of the dataset of interest.

The present inventor has conceived of a flow cytometry system in which the signals from the detectors are provided to both the pulse processor discussed above and a separate, dedicated system (with another pulse processor) that analyzes certain aspects of the signals in real-time or near-real-time in order to provide near-instant insight as to the intensity characteristics of the detector signal, thereby allowing for quicker and more efficient threshold setting, either by a user or by using automated techniques executed, for example, by a processor of a flow cytometry system.

FIG. 1 is a schematic block diagram of a triggering system 100 of the present invention. As illustrated in FIG. 1, the detector 102, or a plurality of detectors 102, detect data from the fluorescence or scatter of light in a flow cell or other sampling location of a flow cytometer, for example, as more specifically disclosed in U.S. Patent Application Ser. No. 62/204,001, filed Aug. 12, 2015, entitled "Multi-Spectral Filter Profiling and Quality Control for Flow Cytometry," which is specifically incorporated herein, by reference, for all that it discloses and teaches. The output of the detector 102 is a detector signal 104 that includes a height signal and a noise signal, both of which are transmitted to a first pulse processor 106 and a second pulse processor 120. As used herein, "height signal" refers to the portion of the detector signal that is "desired," whereas the "noise signal" refers to the portion of the detector signal that is "undesired." It is to be understood that there the portion of the detector signal that is desired, i.e., the height signal, may include contributions from undesired sources. For example, high-intensity fluorescence from a particle of interest may be detected by a photodetector at the same time that a lower-intensity amount fluorescence from a piece of debris is detected by that same detector—the resulting detector signal at that moment will thus include contributions from both the particle of interest and the debris. The photodetector reading at that point in time is still of interest, however, as it includes information relating to the particle of interest, and the detector signal intensity at that time would be considered to be "height signal" as opposed to "noise signal." The portion of the detector signal that is undesired, however, may be ignored completely as it is viewed as having little or no useful content, i.e., primarily or completely attributable to noise.

The detector signal 104 may be delivered simultaneously (or near-simultaneously) to two different pulse processors: a first pulse processor 106 and a second pulse processor 120.

The second pulse processor 120 is configured to analyze the detector signal 104, identify pulses in the detector signal 104 that meet a second threshold value 118 (the second threshold value 118 may also be referred to herein as a "trigger threshold value"), and generate a pulse height data signal 122, a pulse width data signal 124, and a pulse area data signal 126 for each of the pulses identified in the detector signal 104 as meeting the second threshold value 118. The pulse height data signal 122, the pulse width data signal 124, and the pulse area data signal 126, or data derived therefrom, may then be forwarded by the second pulse processor 120 to a storage medium of some sort, e.g., non-volatile memory, and/or a processing unit of the flow cytometer for further analysis or post-processing. The second pulse processor 120 is thus responsible for producing data that actually characterizes the particles of interest and that will be stored as analysis data for the samples being analyzed. Generally speaking, the pulses for which the pulse height data signal 122, the pulse width data signal 124, and the pulse area data signal 126 are stored in the storage medium are the "desired" pulses in the detector signal 104, i.e., the pulses that are likely representative of the particles of interest.

In contrast, the first pulse processor 106 (in conjunction with the real-time trigger module 112 and potentially also the threshold selector 116) is configured to perform a much more superficial, in some respects, and specialized form of analysis on the same detector signal 104. The analysis performed by the first pulse processor 106 is performed in parallel with analysis performed by the second pulse processor 120, and the operation of the second pulse processor 120 may be modified based on the results of the analysis performed by the first pulse processor 106. The operation of the first pulse processor 106 (and the real-time trigger module 112 and the threshold selector 116) are discussed in more detail below.

One key difference between the first pulse processor 106 and the second pulse processor 120 is that data from the second pulse processor 120 is generally communicated to a microprocessor-based system that then stores the data for each triggering event on a long-term storage device, e.g., on a hard disk or solid-state drive. The amount of this data, as discussed elsewhere herein, can be extremely large, and the bandwidth of such data streams can be quite taxing on a microprocessor. In contrast, the data that is ultimately generated by the first pulse processor 106 and the real-time trigger module 112 may be much reduced in size and content—this data would not be suitable for actual analysis, but is well-suited for allowing the second threshold value 118 to be more easily set, as will be described in more detail below.

In some implementations, a first threshold value 108 (which may also be referred to herein as a baseline threshold value) to the first pulse processor 106, the first threshold value 108 may be very low, e.g., 0.01% in some embodiments. A 0.01% first threshold value 108 would, for example, generally cause all pulses in the detector signal 104 having a height (or magnitude or intensity) in the bottom 0.01% of the maximum potential (or the average maximum) height that the detector may be able to output to be ignored by the first pulse processor 106. It is to be understood that in actual practice, the threshold values discussed herein may be a bit value, but may be selectable by a user (in a user-selectable threshold scenario) as a percentage, e.g., a percentage of the total measurement range of the detector used. In such instances, the percentage may be converted to a bit value in order to produce the threshold value. For example, if the detector signal is a signed 24-bit data path, it would range from 0 to 8,388,607 in value, and a 0.01% threshold value would cause detector signals with values of 838 or lower to be excluded from pulse processing. Even with such a low threshold value, a substantial amount of noise from the detector signal 104 may be ignored while still accounting for substantially all (or all) of the height signal. For example, the bottom 0.01% of the detector signal 104 may be attributable to electrical noise in the flow cytometer system—such noise will typically not be considered "desirable" and it therefore makes little sense to configure a flow cytometer threshold selector system to waste resources processing such signals (for the purposes of this disclosure, it is to be understood that use of the first threshold value 108 may be optional, even if omitting it is generally viewed as less desirable). The detector signal 104 may include pulses that have a generally Gaussian shape with a height, width, and area, as are determined by the second pulse processor 120, as discussed above. The pulse processor 106, however, simply detects the height, e.g., amplitude or magnitude, of each of the pulses and generates detector data 110. The height may, for example, be a voltage signal or a count signal indicating a relative magnitude of the light detected by the detector. Detector data 110 comprises a digital signal that includes height data that indicates the height of each pulse detected by the first pulse processor 106 (regardless of whether that pulse is considered to be part of the height signal or the noise signal). Pulse processors, such as those described herein, may monitor a signal and detect each time that the signal crosses a threshold; the pulse processor may then, after detecting that the signal has crossed the threshold value, monitor the signal to determine when the signal crosses back over the threshold value to determine the interval in which the signal was higher than the threshold value. The pulse processor may then determine what the highest value of the signal was within that interval in order to identify the pulse height for that pulse. This may be done retrospectively, e.g., by storing the data for the pulse and then reviewing the data to identify the maximum, or by testing each signal value against a stored "current pulse maximum" value that is reset to zero when the threshold value is first crossed. If a current signal value is higher than the stored current pulse maximum, the stored current pulse maximum value may be overwritten by the current signal value—as the pulse increases, the current pulse maximum will repeatedly be updated as higher- and higher-value signal values in the pulse are received; once the pulse starts to decrease, the current pulse maximum value will no longer be updated, and when the detector signal crosses back over the threshold value, the current pulse maximum that is stored for that pulse may be read out as the height signal for that pulse. In some pulse processors, such as the second pulse processor 120 discussed elsewhere herein, the duration of the pulse interval may be determined in order to identify the pulse width. In some implementations, a pulse processor, after determining the pulse height, may evaluate the data within the pulse to determine the width of the portion of the pulse that is above some percentage of the pulse height, e.g., higher than 50% of the pulse height for that pulse. Similarly, once the extent of the pulse is known, the signal data within the pulse may be integrated (or subjected to data analysis that approximates integration) to determine the area under the signal within the pulse. It is to be understood that the first pulse processor 106 may, in the interests of reducing the amount of processing that it must perform, be configured to only determine the height data for the pulses in the detector signal 104. In comparison, the second pulse processor 120 may perform more extensive characterization of the detector signal, e.g., determining the pulse height, pulse width, and pulse area (and potentially further characteristics as well).

Since the first threshold value 108, if used, is very low, noise (background signals) from the detector 102 may be included in the detector data 110. The height data in the detector data 110 can therefore have a very broad range of values. For example, in some applications, the higher value height data in the detector data 110 can be 10,000 times brighter than the lower value height data in the detector data 110. As such, the detector data 110 may be scaled using a logarithmic scale, e.g., by converting the detector data 110 using a logarithmic function. Such logarithmic scaling may have the effect of reducing the data size, as data in both the lower decades and the higher decades of the logarithmic scale may be expressed at a useful resolution with a reduced bit size as compared with equivalent non-logarithmic values. For example, data encoded in a 24-bit signal representing signal values ranging from 0 to 10,000 units may be scaled logarithmically into an 8-bit, four-decade format, with each decade subdivided into 64 signal values. This has the effect of characterizing the signal data while still preserving useful resolution within each decade, which reduces the amount of data handling that must be done downstream of the logarithmic conversion. Such logarithmic conversion of the detector data 110 may be performed, for example, by a real-time trigger module 112, which is configured to scale the detector data 110 logarithmically and then generate periodic histogram data (data from which a histogram may be constructed) based on that logarithmically scaled detector data indicating how may logarithmically scaled height values in the logarithmically scaled detector data 110 within a given period of time fall within each of a plurality of different bins or class intervals of height values. The real-time trigger module 112 is considered to be "real-time" due to the fact that it processes a large amount of data extremely quickly, e.g., at a rate fast enough to avoid the potential for a buffer or memory overflow due to data entering the system faster than it can exit the system.

For example, if the real-time trigger module 112 is configured to produce periodic histogram data for a total of 256 intervals or bins for pulse heights (before logarithmic scaling) of between 1 and 10,000 units, then the lowest-ranked bin or interval would reflect how many (unsealed) pulse heights within the given period of time would be between 1 and 1.04 units, whereas the highest-ranked bin or interval would reflect how many (unsealed) pulse heights within the given period of time are between 9646.62 and 10,000 units. The histogram data produced by the real-time trigger module may then be transmitted or sent to the threshold selector 116, where it may be used to set a second threshold value 118 for the second pulse processor 120. It is to be understood that other forms of scaling may be used as well in order to transform the detector data and reduce the amount of memory that must be used in order to accumulate the periodic histogram data—this example is not intended to be limiting, and other forms of transformation are contemplated as well.

The threshold selector 116 selects the second threshold value 118 at an intensity value that is sufficiently low to capture the least intense height data in the detector signal 104 and high enough to eliminate background noise of the flow cytometer system in the detector signal 104. In some implementations, the threshold selector 116 may select the second threshold value 118 automatically, whereas in some additional or alternative implementations, the threshold selector 116 may select the second threshold value 118 responsive to one or more user inputs. In the latter case, the threshold selector 116 may generate graphical displays based on the periodic histogram data from the real-time trigger module in order to present the periodic histogram data to a user in an intuitive and useful manner. This is described in more detail later in this disclosure. In implementations in which histogram data may be displayed, the flow cytometry system may, of course, include a display device, such as a liquid-crystal display or organic light emitting diode display, to facilitate the presentation of such a histogram representation.

After being selected, the second threshold value 118 may then be applied to the second pulse processor 120 to prevent noise pulses from being logged, recorded, and/or analyzed by the second pulse processor while still ensuring that the pulse height data signal 122, the pulse width data signal 124, and the pulse area data signal 126 for each of the pulses in the detector signal 104 is obtained, stored, and/or analyzed. As mentioned earlier, most flow cytometers have multiple detectors, and each such detector may have its own dedicated second pulse processor 120. In such instances, the second threshold value 118 may be supplied to the second pulse processor 120 that receives the same detector signal 104 that is fed into the first pulse processor 106. When that second pulse processor 120 detects the start and end of a pulse, according to the second threshold value 118, this may be used as a "trigger" that causes data processed by all of the second pulse processors 120 during that interval to be stored in a storage system, e.g., a hard drive or solid state drive, of the flow cytometer. It is also contemplated that multiple threshold values for different detectors could be used in combination to "trigger" recording, e.g., in order to trigger a data recording event, a first detector's signal must meet or exceed a first threshold while a second detector's signal meets or exceeds a second threshold. In theory, every detector could have a corresponding threshold value, and triggering could be configured to occur in any number of circumstances dependent on whether one or more of those threshold values was met or exceeded at a given time.

Figure 2:
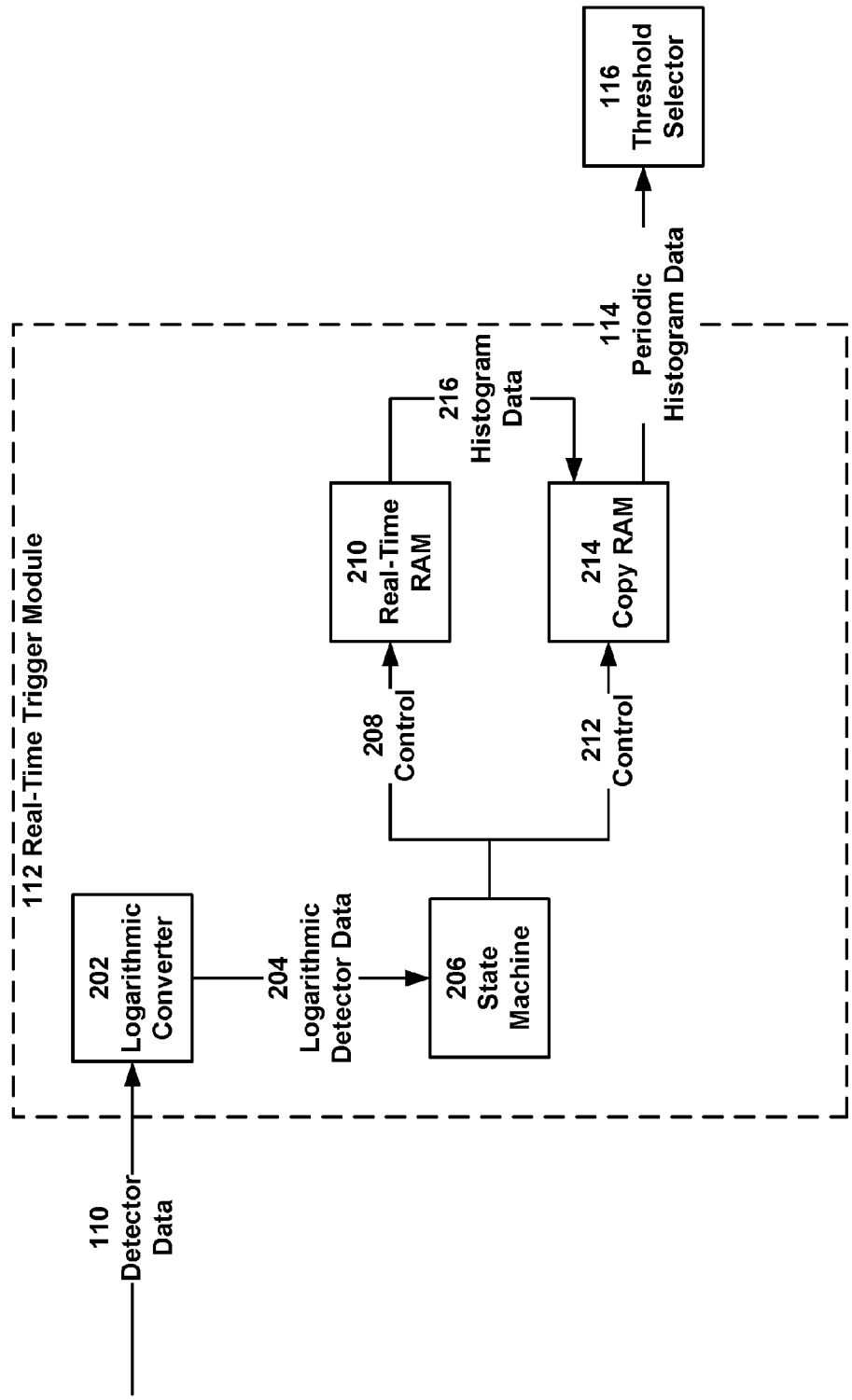
FIG. 2 is a schematic block diagram of an embodiment of a real-time trigger module for use in the triggering system of FIG. 1.

FIG. 2 is a schematic block diagram of one embodiment of the real-time trigger module 112. The detector data 110 is provided to a logarithmic converter 202 of the real-time trigger module 112. The logarithmic converter 202 converts the intensity measurements in the detector data 110 to a logarithmic value; the converted data may be referred to herein as "logarithmic detector data." Generally speaking, the first pulse processor 106 and the real-time trigger module 112 may be implemented as dedicated, special-purpose electronics modules (or as a combined electronics module), e.g., an application-specific integrated circuit (ASIC) or a field-programmable gate array (FPGA), or even potentially a digital signal processor (DSP). The first pulse processor 106 and the real-time trigger module 112 may continually process nearly all of the detector signal/detector data produced by the detector 102 (except for that which is screened out by the first threshold value 108, if used), and since this may require the processing of data streams on the order of 100 MB/s, such dedicated, special-purpose circuits or processors must be used, with respect to the current state of technology, instead of general purpose microprocessor-based systems, e.g., those with operating systems such as Linux or Windows, to avoid situations in which the volume of data being processed overwhelms a non-dedicated processing system.

The logarithmic detector data 204 is then transmitted to state machine 206. The logarithmic detector data 204 is a digital signal that is representative of the detector data that has been converted to a logarithmic scale. The state machine 206 reads the logarithmic detector data 204 for each pulse to determine the logarithmic pulse height value of each pulse, which may be used by the state machine 206 as an address in real-time RAM 210 that is accessed via control signal 208. The state machine 206 may read an occurrence value that is stored at the address indicated by the logarithmic detector data 204 in the real-time RAM 210 and then increment the occurrence value stored in the real-time RAM 210 at that address by a value of one for each pulse having a pulse height value falling within the bin or interval for that address (or for each pulse that has a pulse height matching that address). As such, the real-time RAM 210 accumulates histogram data that indicates the number of occurrences of each pulse height value in the logarithmic detector data 204 falling within the bins or intervals of each address. After the histogram data 216 is accumulated for a predetermined time period, the histogram data 216 may be written to copy RAM 214 at the end that time period. In one implementation, this predetermined time period is on the order of ⅛ of a second so that the histogram data 216 is refreshed 8 times per second. Other predetermined time intervals may be used as well, depending on the desired update frequency for the histogram data. For example, predetermined time periods of $1/16^{th}$ of a second or $1/32^{nd}$ of a second may be used, or other time period durations, e.g., any time periods between $1/32^{nd}$ of a second and one second. Shorter time period durations may also be used, although there may be little utility in such shorter-duration time periods, especially if the threshold selector is to display the histogram data to a user for a user-made selection of a threshold (the human eye would be unable to perceive histogram updates at frequencies higher than about 30 updates per second, so any higher update frequency would be of little or no benefit). After the histogram data 216 is written to the copy RAM 214 at the end of each time period, a control signal 208 sent from the state machine may be used to clear the real-time RAM 210 so that the real-time RAM 210 can begin generating another set of histogram data during the next time period. The copy RAM 214 and the real-time RAM 210 may be provided by different address regions of the same RAM structure or by different RAMs. By building a histogram in the real-time RAM 210 using the intensity (height) of the logarithmic detector data 204 as the address in the real-time RAM, and incrementing the occurrences of the logarithmic detector data 204 stored at the accessed address, greatly reduces the amount of data that is stored in real-time RAM 210 as compared with the amount of data that is normally stored during sample collection and analysis. Thus, the histogram data provides valuable insight as to characteristics of the entire detector signal (minus the portion ignored due to the first threshold value 108, if used) without requiring that all of the detector signal be processed and stored by the flow cytometer; based on the use of this histogram data, the second threshold value 118 may be selected and used to trigger the actual large-scale collection of sample data during operation of the flow cytometer.

Figure 3:
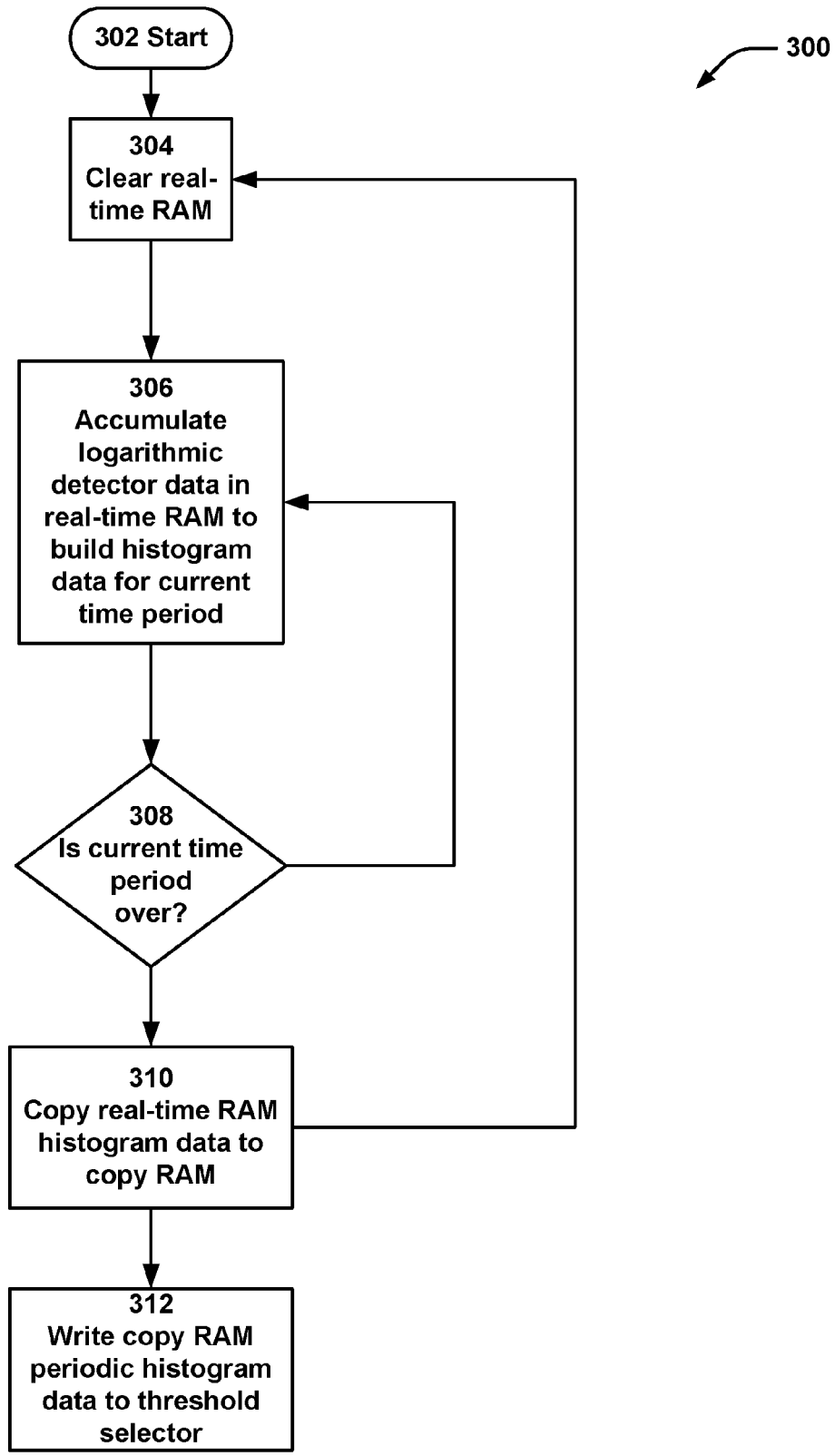
FIG. 3 is an embodiment of a flow diagram that illustrates an embodiment of the operation of the state machine.

The periodic histogram data 114 that is stored in the copy RAM 214 may then be written or passed on to the threshold selector 116. The periodic histogram data 114 may then be used to select the second threshold value 118. The threshold selector 116 does not need to be implemented as part of an FPGA or ASIC, since the periodic histogram data may be very limited in size and bandwidth, allowing it to be passed to a microprocessor-based system without significantly affecting the processing overhead. For example, there may be only 256 integer-type occurrence values for each periodic histogram data set that need to be processed by the threshold selector 116, which is a relatively trivial amount of data compared to the potential datastream that may need to be processed by a flow cytometer's computing system when data from all of the detectors is being stored during a trigger event. As such, the threshold selector 116 may be implemented as a software module that is executed on a general-purpose computer or other microprocessor-based system and that receives periodic histogram data from the real-time trigger module 112 that is implemented on an FPGA, ASIC, or DSP. It is also envisaged that the threshold selector 116 may be implemented using an FPGA, ASIC, or DSP (it could even be part of the same processing circuitry that is used to provide the first pulse processor 106 and the real-time trigger module 112), in which case it may operate completely independently of a microprocessor-based system that is used to operate the flow cytometer and store test results. It is also to be understood that the real-time trigger module 112 and/or the first pulse processor 106 may, as processing capabilities of microprocessor-based systems continue to improve, potentially be implemented using microprocessor based systems (as opposed to using an ASIC-, FPGA-, or DSP-based approach) if microprocessor speeds increase to the point where handling data streams on the order of 100 MB/s or more for extended periods of time are no longer infeasible. FIG. 3 is a schematic block diagram 300 that illustrates one embodiment of the operation of the state machine 206. The operation of the state machine starts at step 302. At step 304, the state machine clears the real-time RAM 210 by writing zeros to all of the memory locations in the real-time RAM 210. At step 306, the occurrences of the logarithmic detector data 204 with detected pulse heights falling within each bin or interval is accumulated in the corresponding addresses of the real-time RAM 210 so that the real-time RAM 210 builds the histogram data for the current time period. At step 308, it is determined whether the current time period has expired. If the current time period has not expired, the process continues by accumulating the occurrences of pulse heights falling within the bins or intervals associated with each RAM address in the real-time RAM so that the histogram data continues to have data points added to it. When it is determined that the current time period is over, the process proceeds to step 310. In a flow cytometer, a typical time period duration may be an eighth of a second. At step 310, the histogram data 216 is copied to the copy RAM 214 at the end of the current time period. This process occurs at the end of each time period. At step 312, the periodic histogram data 114 stored in the copy RAM 214 may be written or sent to the threshold selector 116. It should be noted that the first pulse processor 106 and real-time trigger module 112, due to being implemented as application-specific circuits or field-programmable gate arrays that operate independently of the pulse processor 120, may operate at a very high speed, e.g., 1,000,000 detected pulses per second, that allows for the height characteristics of all of the pulses in the detector signal (minus those pulses that may be discarded due to the first threshold value 108) to be accounted for in the histogram data. If this same data were to be obtained from the pulse processor 120 and extracted by software run by a microprocessor or processor of the flow cytometer, the amount of data that would need to be handled to consider every data pulse would rapidly exceed the capabilities of such a microprocessor or processor's ability to process.

Figure 4:
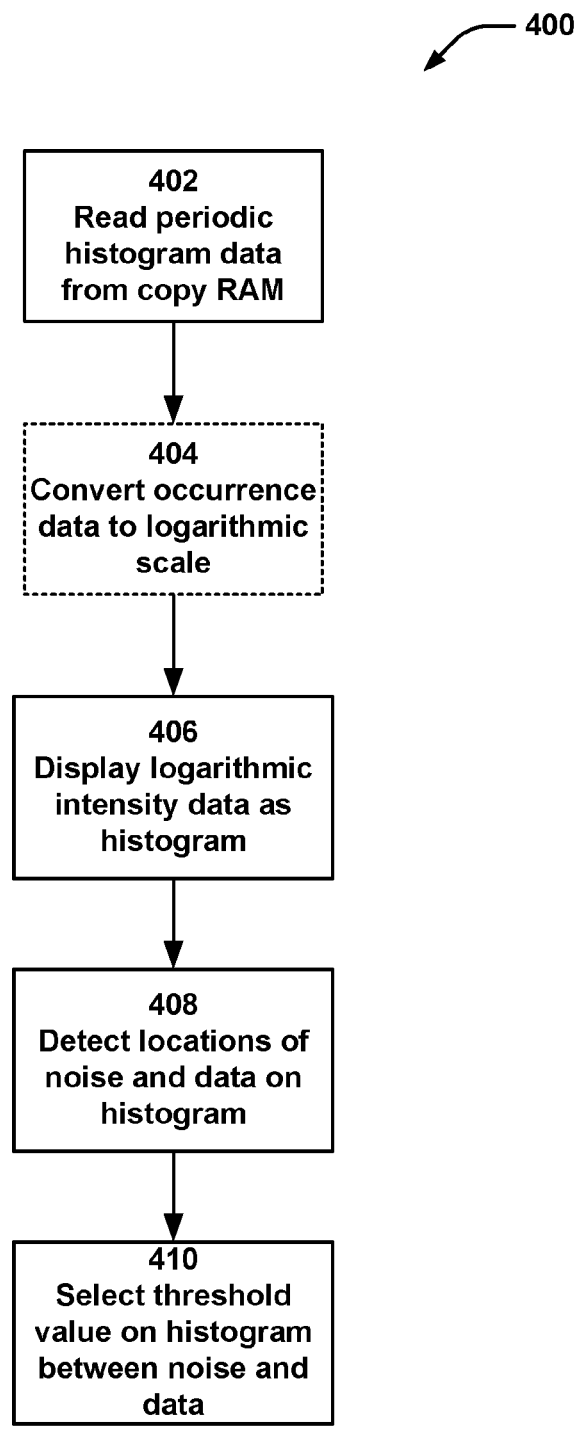
FIG. 4 is an embodiment of a flow diagram of the operation of the threshold selector of the embodiment of FIG. 1.

FIG. 4 is a flow diagram 400 which illustrates one embodiment of the operation of threshold selector 116. At step 402, the threshold selector 116 reads the periodic histogram data 218 from the copy RAM 214. In step 404, which is optional, the occurrence data in the histogram data may be converted to a logarithmic scale. Converting the occurrence data in the histogram data to a logarithmic scale may be beneficial in situations where the histogram data is to be presented to a human operator and where there are one or more magnitudes more of variation in the occurrence data. The intensity data was already converted to a logarithmic scale by the logarithmic converter 202, which is plotted in the graphs illustrated in FIGS. 7, 8 and 9, along the horizontal axes of the graphs; the vertical axes of the graphs represent the occurrence data for each logarithmic intensity. If the occurrence data is to be displayed as a histogram or other visual format for display to a human operator, the occurrence data also may be converted to a logarithmic scale, as discussed above, especially if a large amount of data is going to be included in each of the histograms. At step 406, the logarithmic occurrence data and logarithmic intensity data may be displayed as a histogram to facilitate allowing a user to manually set a threshold value based on the histogram data. At step 408, the locations for the noise and the data are detected on the histogram. At step 410, the threshold value is selected on the histogram between the noise and the data. The selection can be done in various ways including various pattern recognition techniques and other recognition techniques that are capable of distinguishing between the data and the noise; for example, any of a variety of different cluster detection or deconvolution techniques may be used to distinguish between data and noise in the histogram data. Alternatively, the threshold may be selected by a user using a GUI or other interface that allows the user to specify the threshold and that also conveys the histogram data to the user, e.g., via a display of a histogram.

As is evident from the above discussion, the ultimate output resulting from the first pulse processor 106 and the real-time trigger module 112 is periodic histogram data. This data, while describing a very data-rich signal (the detector signal 104), is much smaller in size than the detector signal 104. For example, for each histogram period, the dataset that is read from the copy RAM 214 will consist of a fixed number data points—the number of data points for each data set will correspond with the number of bins or intervals in the histogram, and each data point will have a corresponding integer value that indicates the number of occurrences for that bin or interval.

Figure 5:
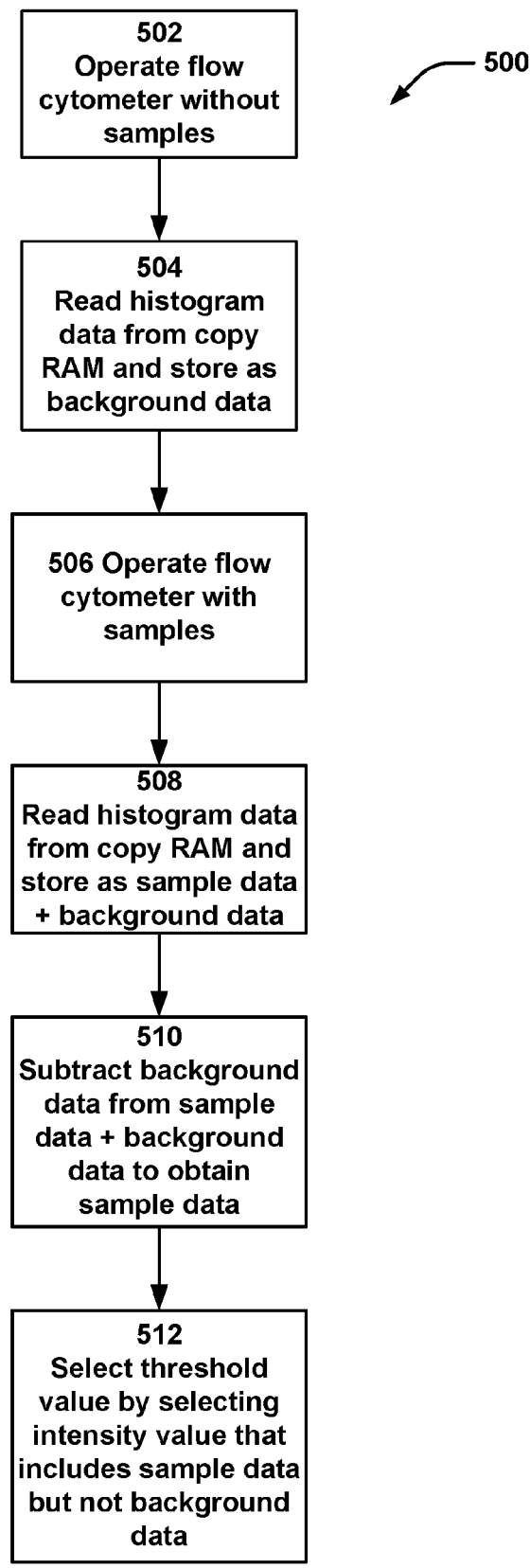
FIG. 5 is another embodiment of a flow diagram for the operation of the threshold selector of FIG. 1.

FIG. 5 is a flow diagram 500 that illustrates another embodiment of the operation of the threshold selector 116. At step 502, the flow cytometer is operated without any samples. The output of the flow cytometer, consequently, does not include sample data but only includes background noise. The occurrence data associated with the background noise is then read from the copy RAM 214 and stored in threshold selector 116 at step 504. At step 506, the flow cytometer is then operated with samples. The signals generated by the flow cytometer therefore include data arising from both the background noise and the samples. The occurrence data/histogram data arising from such signals is then stored in the copy RAM. At step 510, the threshold selector may subtract the background noise occurrence data stored previously from the combined noise+sample occurrence data to lessen the contribution of the "noise" occurrences to the histogram data used by the threshold selector. A threshold value can then be selected by selecting an intensity value in the histogram that divides sample data and the background noise (despite the "removal" of noise occurrence data, there may, for example, still be noise occurrence data that is attributable to noise within the sample itself, such as debris in the sample fluid that was not present when the flow cytometer was operated without any samples). This can be done by recognition of the profile of the noise data or the sample data.

Figure 6:
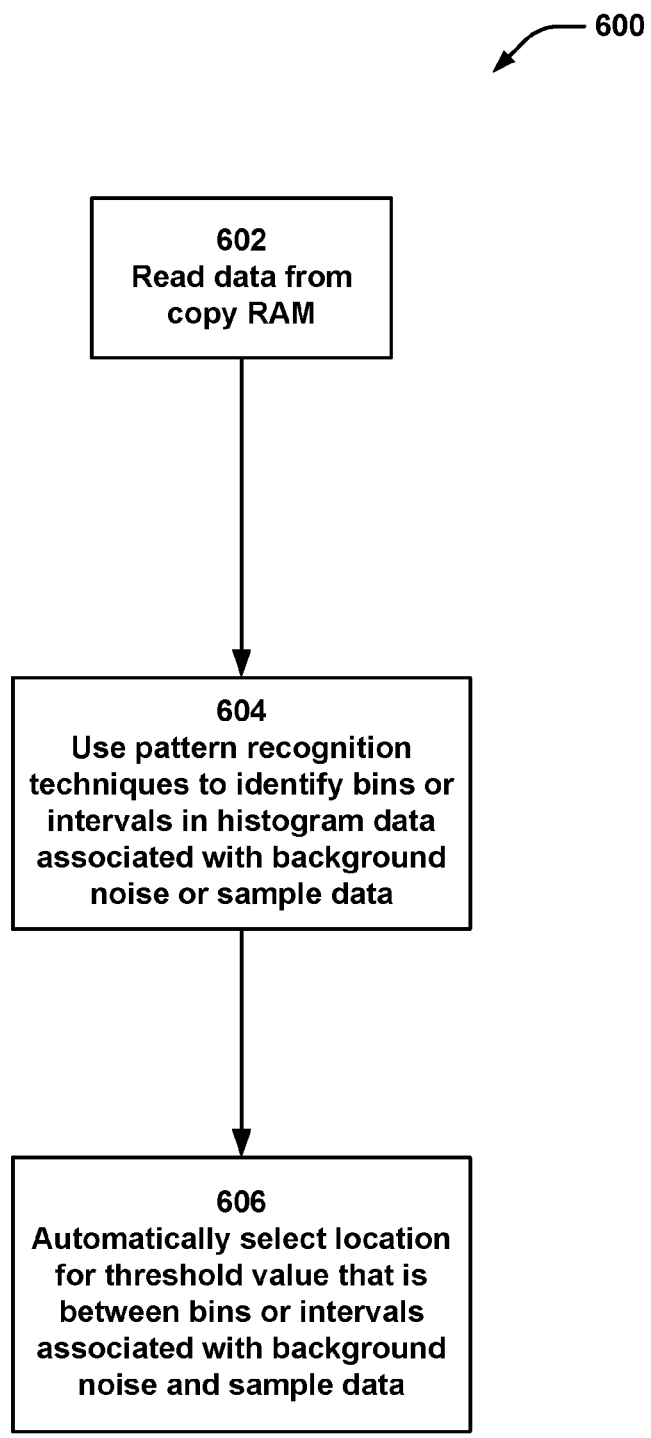
FIG. 6 is a flow diagram of yet another embodiment for the operation of the threshold selector of FIG. 1.

FIG. 6 is a flow diagram 600 of another embodiment of the operation of the threshold selector 116. At step 602, the occurrence data is read from the copy RAM 214. At step 604, pattern recognition techniques are used to identify locations of intensity on the axis between the background noise and the sample data. At step 606, a location is automatically selected on the intensity axis between the locations of the background noise and the sample data for use as a threshold signal.

Figures 7, 8, 9:
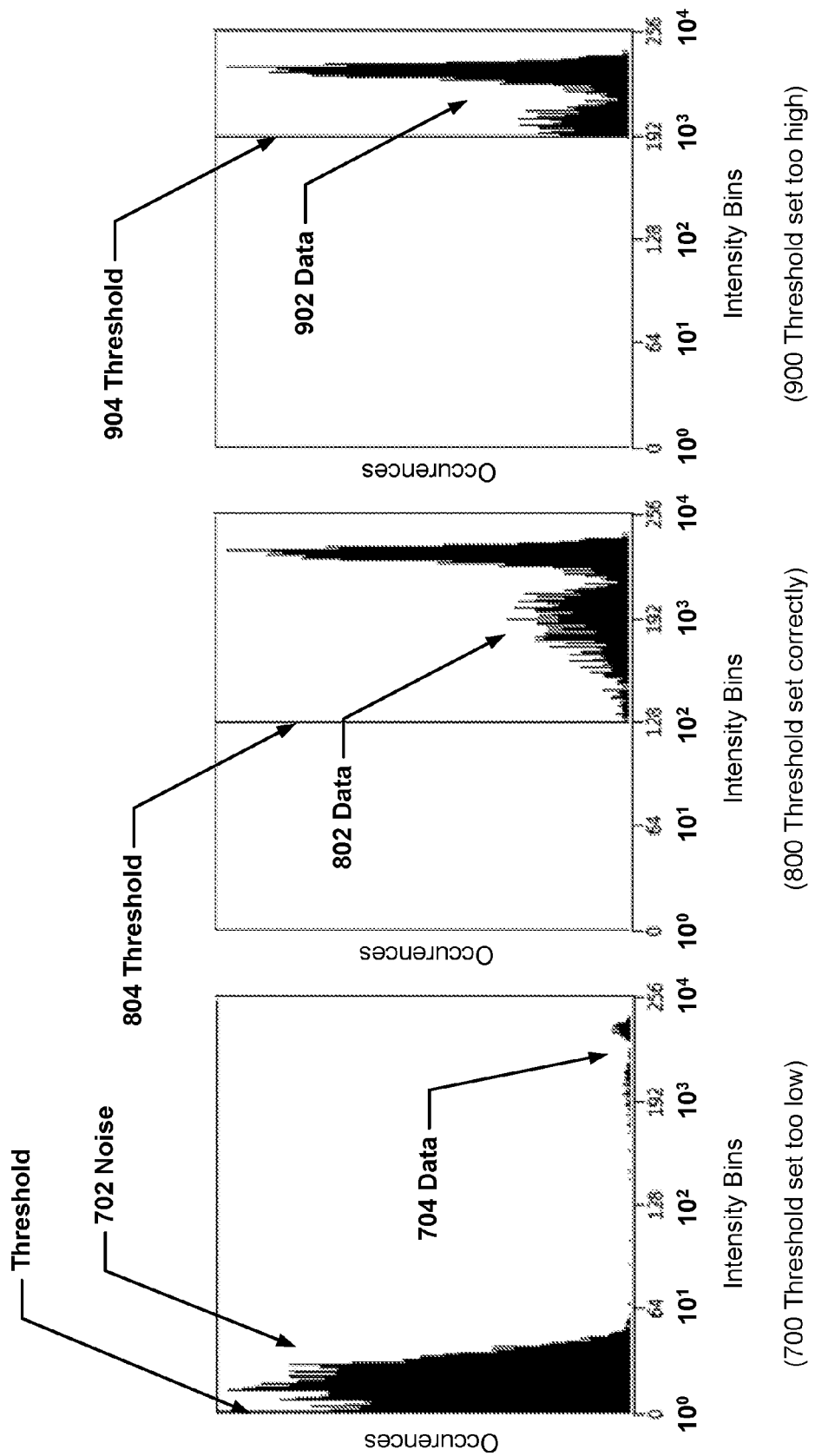
FIGS. 7, 8 and 9 are histograms illustrating various thresholds that are applied to a detector signal.

FIGS. 7, 8, and 9 are histograms with the intensity data binned along the axis and the number of occurrences of signals falling within each intensity bin on the ordinate. Both the intensity and the occurrences are plotted on a logarithmic scale so that the histograms of FIGS. 7, 8, and 9 can be meaningfully interpreted by a user.

As shown in FIG. 7, the threshold 706, which is equivalent to the second threshold 118, is set at a very low value or zero such that the noise signal 702 is much higher than the data signal 704. As shown in FIG. 8, the threshold 804, which is equivalent to the second threshold 118, is set at a location between the noise signal 702 of FIG. 7 and the data signal 704 of FIG. 7. As such, the noise signal 702 is eliminated from the stream of data. FIG. 9 illustrates the setting of a threshold 904, which is equivalent to the second threshold 118, at too high of an intensity level. Only a portion of the data 902 exists when the threshold 904 is applied at the high intensity as illustrated in FIG. 9. As such, a portion of the data 902 is missing from the output. It is to be understood that FIGS. 7, 8, and 9 are histograms of the intensity data (pulse height data) that is produced by the second pulse processor 120, and not the first pulse processor 106—the first pulse processor 106 is not affected by the second threshold value 118, so the histogram data that is generated based on data from the first pulse processor 106 would not exhibit the absence of data below the indicated thresholds.

Figure 10:
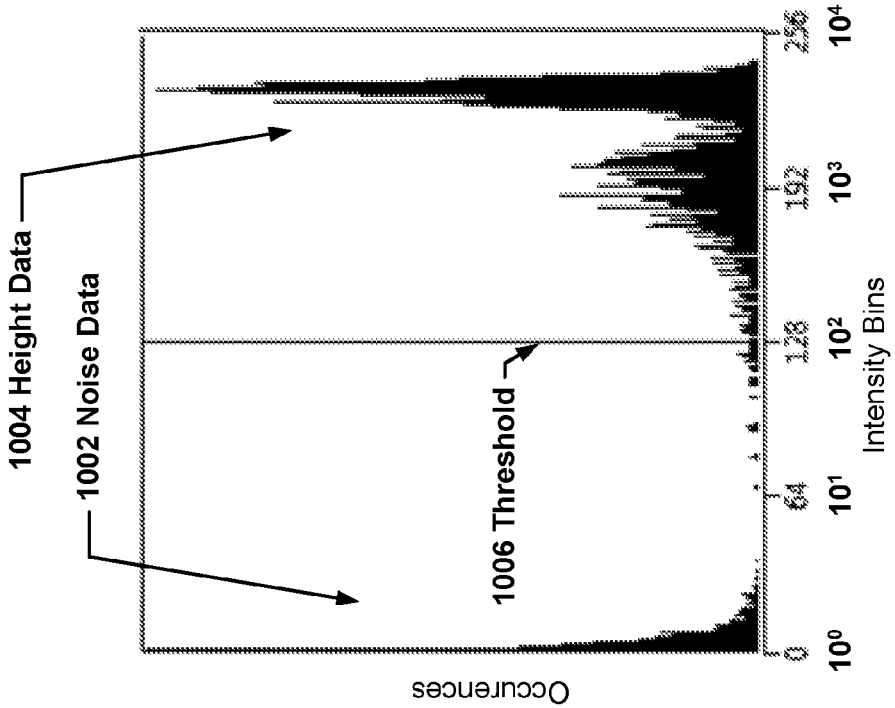
FIG. 10 is a histogram illustrating the placement of a threshold between noise signals and detector height data.

FIG. 10 is a histogram of the number of occurrences of the detector signals versus the intensity of the detector signals. The detector signal includes the noise data 1002 and the height data 1004. FIG. 10 is an example of an interface that may be used to allow a user to select an appropriate second threshold value 118—as can be seen, the occurrence data for all of the intensity values on the horizontal axis is shown (based on the periodic histogram data provided by the real-time trigger module 112), as is a vertical line indicating the current setting of the second threshold value, e.g., threshold 1006. The interface may be configured to allow the user to move the position of the threshold 1006, e.g., by clicking and dragging it or by incrementing, decrementing, or otherwise changing a value (not displayed) that governs where the threshold 1006 is located. As shown in FIG. 10, the noise data 1002 primarily occupies the low intensity portions of the histogram 1000. The height data 1004 occupies the portion of the histogram that has higher intensities. Consequently, selection of the location on the intensity scale for the threshold 1006 is rather straightforward. However, in some instances, the height data 1004 may be present at lower intensities and may overlap the noise data 1002. In that case, the flow cytometer can be operated without samples to determine the location and profile of the noise data 1002. Once the profile of the noise data 1002 is identified, a location on the intensity scale of the histogram of FIG. 10 can be selected so that noise data 1002 can be substantially eliminated from the height data 1004.

Figure 11:
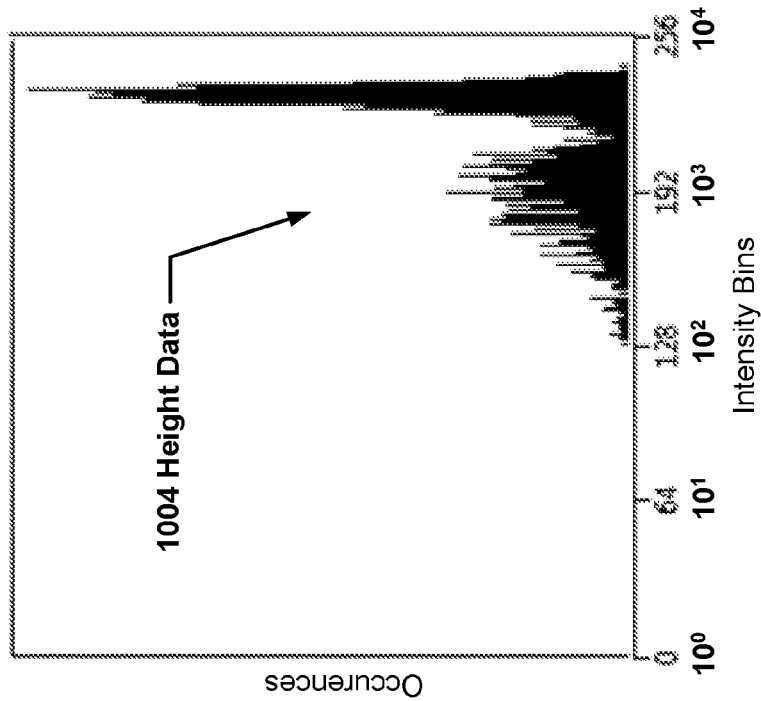
FIG. 11 is a histogram illustrating the removal of noise using the threshold of FIG. 10.

FIG. 11 is a histogram that illustrates the application of the threshold 1006 to the noise data 1002 and height data 1004 that is produced by the second pulse processor and that is then stored by the flow cytometer. As illustrated in FIG. 11, all of the signals below the threshold 1006 have been eliminated, which leaves strictly the height data 1004 in the histogram of FIG. 11. This threshold 1006 can thus be used with the second pulse processor 120 (FIG. 1) so that the noise data can be eliminated from the detector signal 104 to provide a pulse height data signal 122, a pulse width data signal 124, and a pulse area data signal 126 for each desired pulse in the detector signal 104 with little or no noise, e.g., to capture the pulses that correlate with the occurrence data on the right side of the threshold 1006.

Figure 12:
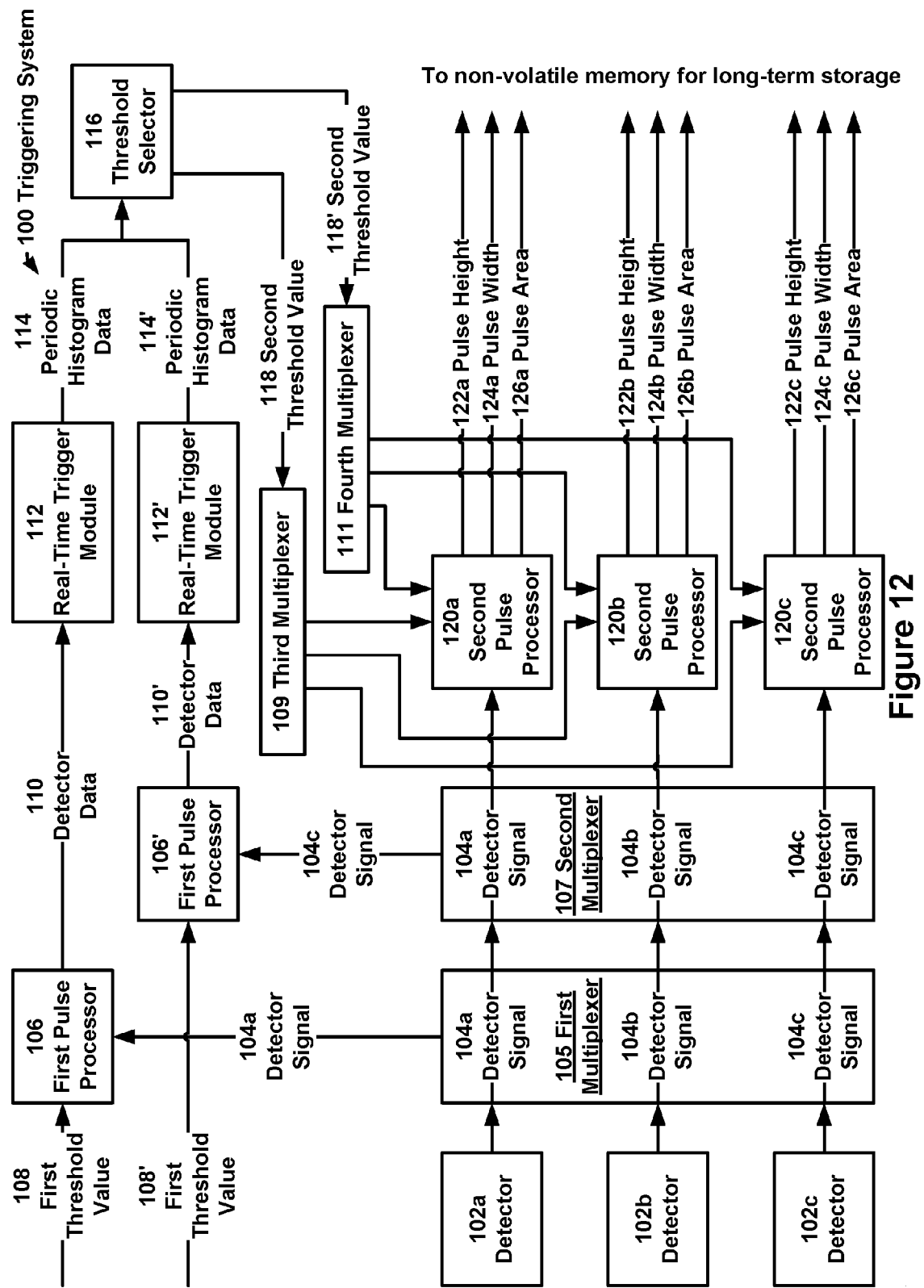
FIG. 12 is a schematic block diagram of another embodiment of a triggering system for use with a flow cytometer.

FIG. 12 depicts a block diagram of another implementation of a triggering system. This triggering system includes many of the elements discussed earlier with respect to the triggering system of FIG. 1, but is configured to allow two separate second threshold values to be set, each for a separate second pulse processor. This example triggering system is also configured to allow the detectors that provide the data to the different first pulse processors to be user-selected.

As can be seen in this example triggering, there are three detectors 102-102*a*, 102*b*, and 102*c*—that each provide a corresponding detector signal 104*a*, 104*b*, and 104*c*, respectively, to a first multiplexer 105 and a second multiplexer 107. The first multiplexer 105 and the second multiplexer 107 may each have an output that may be switched between any of the detector input channels to allow the detector signal 104 from any desired detector to be routed to the first pulse processor 106 or the first pulse processor 106', respectively. In this example, the first multiplexer 105 has been set to provide the detector signal 104*a* from the detector 102*a* to the first pulse processor 106, and the second multiplexer 107 has been set to provide the detector signal 104*c* from the detector 102*c* to the first pulse processor 106'. It is to be understood that this multiplexer approach may also be used for flow cytometers having only one first pulse processor and real-time trigger module but multiple detectors—in such cases, this allows the user to select which of the detectors will be used with the triggering system.

The first pulse processors 106 and 106' may each correspondingly be supplied with first threshold values 108 and 108', respectively, which may be set quite low (as with the first threshold value 108 in FIG. 1) to screen out very low-intensity pulse height data. The first pulse processors 106 and 106' may then each generate detector data 110 and 110', respectively, which may then be passed to real-time trigger modules 112 and 112', respectively. The real-time trigger modules 112 and 112' may then provide periodic histogram data 114 and 114' to the threshold selector 116, which may then either analyze the periodic histogram data to automatically select second threshold values 118 and 118' or present a visual plot based on the two separate sets of periodic histogram data 114 and 114' to allow a user to make an informed decision as to where to set the second threshold values 118 and 118'.

Once the second threshold values 118 and 118' have been set, each second threshold value 118 and 118' may be provided to the appropriate second pulse processor 120—in this example, second pulse processor 120*a*, 120*b*, or 102*c*. Thus, for example, the second threshold value 118 may be supplied to the second pulse processor 120 that processes the same detector signal on which selection of the second threshold value was based—in this example, the second threshold value 118 would be supplied to the second pulse processor 120*a* since the second pulse processor 120*a* processes the detector signal 104*a*. Correspondingly, the second threshold value 118' would be supplied to the second pulse processor 120*c* since the second pulse processor 120*c* processes the detector signal 104*c*. Since the detector signals 104 for each first pulse processor 106 may be user-selectable using, for example, multiplexers 105 and 107, the second threshold values 118 and 118' may correspondingly be appropriately routed to the correct second pulse processors 120 and 120' using, for example, third multiplexer 109 and fourth multiplexer 111, which may allow each second threshold value to be independent routed to an appropriate second pulse processor.

It is to be understood that while this example shows only three detectors and two first pulse processors/real-time trigger modules, the principles discussed herein may be applied in systems having any number of detectors and/or first pulse processors/real-time trigger modules. At some point, however, the number of variables to consider in setting a second threshold value may become too overwhelming to be useful (at least, for human operators) if too many first pulse processors/real-time trigger modules are used in the determination of the second threshold values.

The triggering system may be configured such that the second threshold value 118 and 118' may control how triggering of all of the second pulse processors is to occur, i.e., to control when data is committed to long-term storage for later analysis and review. The triggering system may support a variety of different trigger conditions—for example, one common trigger condition is to require that the second threshold value 118 be met or exceeded at the same time that the second threshold value 118' is met or exceeded (a logical "AND" condition). This may be used when a particular desired sample, for example, fluoresces at two different wavelengths simultaneously, and where other particles in the sample that are viewed as noise may fluoresce in only one of those wavelengths (or perhaps in both wavelengths, but not simultaneously for a given particle). Another trigger condition may be that the second threshold value 118 be met or exceeded or the second threshold value 118' be met or exceeded (a logical "OR" condition). This may be useful in situations where there are two different types of particles for which data is desired—each particle may fluoresce at a different wavelength. A further trigger condition may be that the second threshold value 118 be met or exceeded at the same time that the second threshold value 118' is not met or exceeded. Generally speaking, the triggering condition may be a Boolean statement involving the different threshold evaluations and one or more Boolean operators, e.g., an AND operator, an OR operator, or a NOT operator (e.g., NOT pulse height≥second threshold value 118 AND additional pulse height≥second threshold value 118').

For example, the Boolean statement/conditions may be any of the statements listed in the table below, where "trigger threshold" refers to the second threshold value 118 and "additional trigger threshold" refers to the second threshold value 118'.

Figure 13:
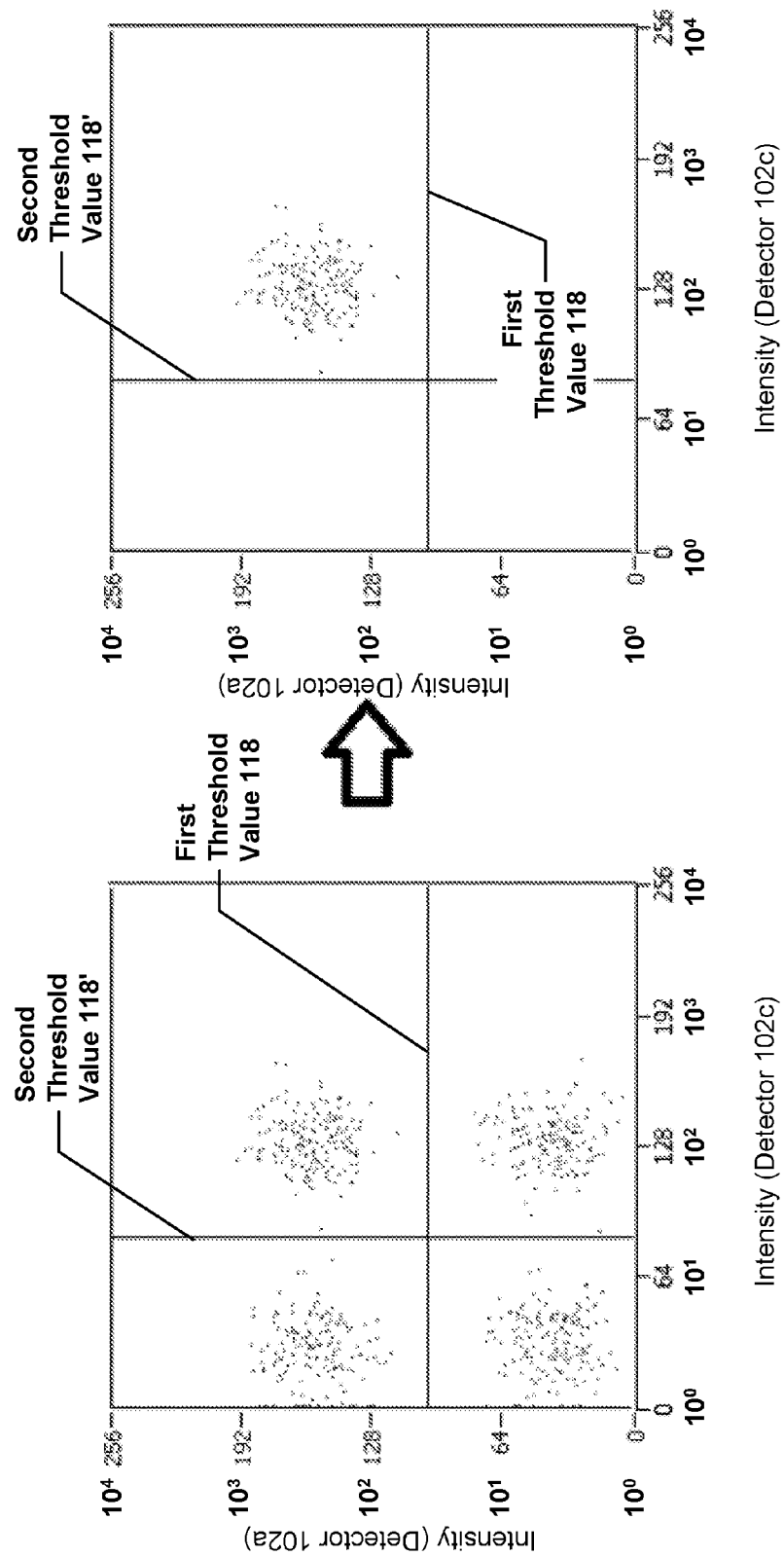
FIG. 13 depicts density plots that may be produced by the threshold selector of the system of FIG. 12.

Trigger Threshold Met or Exceeded OR Additional Trigger Threshold Met or Exceeded
Trigger Threshold Met or Exceeded OR Additional Trigger Threshold NOT Met or Exceeded
Trigger Threshold NOT Met or Exceeded OR Additional Trigger Threshold Met or Exceeded
Trigger Threshold NOT Met or Exceeded OR Additional Trigger Threshold NOT Met or Exceeded
Trigger Threshold Met or Exceeded AND Additional Trigger Threshold Met or Exceeded
Trigger Threshold Met or Exceeded AND Additional Trigger Threshold NOT Met or Exceeded
Trigger Threshold NOT Met or Exceeded AND Additional Trigger Threshold Met or Exceeded
Trigger Threshold NOT Met or Exceeded AND Additional Trigger Threshold NOT Met or Exceeded Once the triggering condition, whatever it may be, is met for a given pulse, the second pulse processors 120a, 120b, and 120c may all be caused to provide pulse height data signals 122a, 122b, and 122c; pulse width data signals 124a, 124b, and 124c; and pulse area data signals 126a, 126b, and 122d, respectively for the duration of the pulse; this data may be provided to a non-volatile data storage system or data storage device, e.g., sent to a microprocessor-based computing system that stores the data to a hard drive or a solid state drive. FIG. 13 depicts an example of a histogram-type plot (left side) that may be produced by the threshold selector 116 of the embodiment shown in FIG. 12; the plot on the right side indicates the intensity data for the data produced by the second pulse processors 120a and 102c after the second threshold values 118 and 118' have been applied to the detectors 102a and 102c (in an AND fashion). In this example, the periodic histogram data is presented as a two-axis density plot with the horizontal axis correlating with the pulse height of the detector signal from detector 102a and the vertical axis correlating with the pulse height of the detector signal from detector 102c. Each XY location in this plot represents a different combination of intensities of the two detector signals for a given pulse. Given the two-dimensional nature of this data, the occurrences of each particular combination of intensities may be relatively infrequent, although a large cluster of occurrences in a given area (as shown in the left-hand plot of FIG. 13, there are four distinct clusters of different XY occurrences) may allow desired signal to be differentiated from undesired signal. In some implementations, the points may be color-coded to indicate the number of times particular XY intensity combinations occur, e.g., darker-colored points may indicate a greater number of occurrences than lighter-colored points. The first threshold value 118 may be used to set the threshold for the detector 102a in this example, and the first threshold value 118' may be used to set the threshold for the detector 102c.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A flow cytometry apparatus comprising:
   a detector configured to produce a detector signal responsive to detecting light during operation of the flow cytometer;
   a first pulse processor configured to receive the detector signal from the detector and to output detector data characterizing pulse heights of pulses in the detector signal;
   a second pulse processor configured to also receive the detector signal from the detector and to output a pulse height data signal, a pulse width data signal, and a pulse area data signal for desired pulses in the detector signal, wherein, for each desired pulse:
      the second pulse processor is configured to output the pulse height data signal, the pulse width data signal, and the pulse area data signal for that desired pulse responsive to a set of one or more trigger conditions being met, and
      the set of one or more trigger conditions at least includes a trigger condition involving a comparison of the pulse height for that desired pulse with a trigger threshold value;
   a real-time trigger module configured to receive the detector data from the first pulse processor and to generate periodic histogram data from the detector data; and
   a threshold selector configured to receive the periodic histogram data from the real-time trigger module and to provide the trigger threshold value.

2. The flow cytometry apparatus of claim 1, wherein the set of one or more trigger conditions is met for each desired pulse when the pulse height for that desired pulse meets or exceeds the trigger threshold value.

3. The flow cytometry apparatus of claim 1, wherein the first pulse processor is configured to output the detector data characterizing the pulse height of the pulses in the detector signal only for pulses that meet or exceed a baseline trigger value.

4. The flow cytometry apparatus of claim 1, further comprising a data storage device, wherein the flow cytometry apparatus is configured to store the pulse height data signal, the pulse width data signal, and the pulse area data signal output by the second pulse processor on the data storage device.

5. The flow cytometry apparatus of claim 4, wherein data from the first pulse processor is not stored on the data storage device.

6. The flow cytometry apparatus of claim 1, further comprising:
   one or more additional detectors; and
   one or more additional second pulse processors, wherein:
      each additional detector is configured to produce a corresponding additional detector signal responsive to detecting light during operation of the flow cytometer, and
      each additional second pulse processor is associated with a different one of the one or more additional detectors and is configured to receive the corresponding additional detector signal from that additional detector and to output at least a corresponding additional pulse height data signal, a corresponding additional pulse width data signal, and a corresponding additional pulse area data signal responsive to each time the set of one or more trigger conditions is met.

7. The flow cytometry apparatus of claim 6, further comprising:

an additional first pulse processor configured to receive the corresponding additional detector signal from a particular one of the one or more additional detectors and to output additional detector data characterizing pulse heights of pulses in that corresponding additional detector signal; and an additional real-time trigger module configured to receive the additional detector data from the additional first pulse processor and to generate additional periodic histogram data from the additional detector data, wherein:

the threshold selector is further configured to receive the additional periodic histogram data from the additional real-time trigger module and to provide an additional trigger threshold value, and the set of one or more trigger conditions further includes a trigger condition involving a comparison of a pulse height in the corresponding additional detector signal from the particular one of the one or more additional detectors with the additional trigger threshold value.

8. The flow cytometry apparatus of claim 7, wherein the set of one or more trigger conditions is met for each desired pulse when:

the pulse height for that desired pulse meets or exceeds the trigger threshold value, and the pulse height in the corresponding additional detector signal from the particular one of the one or more additional detectors meets or exceeds the additional trigger threshold value during that desired pulse.

9. The flow cytometry apparatus of claim 7, wherein the set of one or more trigger conditions is met for each desired pulse when a logic statement evaluates to true, the logic statement involving one or more Boolean operators, an evaluation of whether the pulse height for that desired pulse met or exceeded the trigger threshold value, and an evaluation of whether the pulse height in the corresponding additional detector signal from the particular one of the one or more additional detectors met or exceeded the additional trigger threshold value during that desired pulse, wherein the one or more Boolean operators are selected from the group consisting of an AND operator, an OR operator, a NOT operator, and combinations thereof.

10. The flow cytometry apparatus of claim 1, wherein the real-time trigger module includes:

a logarithmic converter;
a state machine;
a first RAM; and
a second RAM, wherein:
the logarithmic converter is configured to convert the detector data into logarithmic detector data,
the first RAM stores occurrence values,
each occurrence value is associated with a different logarithmic pulse height value contained within the logarithmic detector data, and
the state machine is configured to:
determine the logarithmic pulse height value for each pulse of the pulses represented in the logarithmic detector data during a first predetermined time period,
cause, for each logarithmic pulse height value that is determined, the occurrence value associated with that logarithmic pulse height value to be incremented by one, and
cause the occurrence values stored in the first RAM at the end of the first predetermined time period to be copied to the second RAM and, subsequent to causing the occurrence values stored in the first RAM to be copied to the second RAM, cause the occurrence values stored in the first RAM to be re-set.

11. The flow cytometry apparatus of claim 1, further comprising a display device, wherein the threshold selector is configured to:

present the periodic histogram data on the display device,
receive an input indicating a value for the trigger threshold value, and
use the value indicated by the input as the trigger threshold value.

12. The flow cytometry apparatus of claim 11, further comprising a memory, wherein the threshold selector is configured to:

store occurrence values in the memory that are representative of one or more first instances of the periodic histogram data as a background noise template, and
subtract the occurrence values of the background noise template from corresponding occurrence values in one or more second instances of the periodic histogram data generated after the one or more first instances of the periodic histogram data before presenting the one or more second instances of the periodic histogram data on the display device.

13. The flow cytometry apparatus of claim 1, wherein the threshold selector is configured to automatically select the trigger threshold based on the periodic histogram data.

14. The flow cytometry apparatus of claim 13, wherein the threshold selector is configured to automatically select the trigger threshold by applying one or more pattern recognition techniques to the periodic histogram data.

15. The flow cytometry apparatus of claim 1, wherein the real-time trigger module is implemented in a field-programmable gate array or an application-specific integrated circuit.

16. A method for operating a flow cytometry system, the method comprising:

detecting light using a detector during operation of the flow cytometer;
providing a detector signal from the detector to a first pulse processor configured to receive the detector signal;
causing the first pulse processor to output detector data characterizing pulse heights of pulses in the detector signal;
causing a real-time trigger module configured to receive the detector data from the first pulse processor to generate periodic histogram data from the detector data;
causing a threshold selector configured to receive the periodic histogram data from the real-time trigger module to provide a trigger threshold value; and
causing a second pulse processor configured to also receive the detector signal from the detector to output a pulse height data signal, a pulse width data signal, and a pulse area data signal for desired pulses in the detector signal, wherein, for each desired pulse:
the pulse height data signal, the pulse width data signal, and the pulse area data signal for that desired pulse are only output responsive to a set of one or more trigger conditions being met, and the set of one or more trigger conditions at least includes a trigger condition involving a comparison of the pulse height for that desired pulse with the trigger threshold value.

17. The method for operating a flow cytometry system of claim 16, the method further comprising:

storing the pulse height data signal, the pulse width data signal, and the pulse area data signal for the desired pulses on a non-volatile storage device.

18. The method for operating a flow cytometry system of claim 17, the method further comprising:

discarding the detector data processed by the real-time trigger module without storing that data on the non-volatile storage device.

19. The method for operating a flow cytometry system of claim 16, the method further comprising:

causing the threshold selector to display a histogram based on the periodic histogram data and a visual indicator on the histogram of the trigger threshold value.

* * * * *